United States Patent [19]

Lunsford et al.

[11] Patent Number: 4,609,735

[45] Date of Patent: Sep. 2, 1986

[54] CERTAIN ARYLOXY-4-CHLORO-2-BUTANOL INTERMEDIATES

[75] Inventors: Carl D. Lunsford; Ying-Ho Chen, both of Richmond, Va.

[73] Assignee: A. H. Robins Company, Inc., Richmond, Va.

[21] Appl. No.: 649,333

[22] Filed: Sep. 11, 1984

Related U.S. Application Data

[60] Division of Ser. No. 418,940, Sep. 16, 1982, abandoned, which is a division of Ser. No. 813,056, Jul. 5, 1977, Pat. No. 4,379,167, which is a continuation-in-part of Ser. No. 730,498, Oct. 17, 1976, abandoned, which is a continuation-in-part of Ser. No. 618,984, Oct. 2, 1975, abandoned, which is a continuation-in-part of Ser. No. 518,122, Oct. 25, 1974, abandoned.

[51] Int. Cl.$^4$ .................. C07D 213/64; C07C 103/38; C07C 49/82; C07C 43/23
[52] U.S. Cl. .................................... 546/302; 568/337; 568/643; 568/649; 564/223
[58] Field of Search ....................... 568/643, 649, 337; 564/223; 546/302

[56] References Cited

U.S. PATENT DOCUMENTS 2,260,753 10/1941 Marple et al. ........................ 568/649

OTHER PUBLICATIONS

Misti et al., Chemical Abstracts, vol. 60, (8), pp.-9268-g to 9269-e, Apr. 13, 1964.

*Primary Examiner*—Alan L. Rotman

[57] ABSTRACT

Novel 1-aryloxy-4-amino-2-butanols of the formula

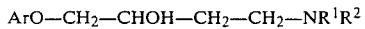

$$ArO-CH_2-CHOH-CH_2-CH_2-NR^1R^2$$

wherein AR is 1-naphythyl, 2-naphthyl, indene-4(or 5-)yl, 3-(or 5-)chloro-2-pyridyl, phenyl, monosubstituted phenyl or di-substituted phenyl, $R^1$ is lower alkyl, phenyl, phenylalkyl, 2-hydroxymethyl-2-propyl, adamantyl or lower-cycloalkyl, $R^2$ is hydrogen or lower alkyl, wherein $R^1$ and $R^2$ together with the adjacent nitrogen form a heterocyclic residue and the pharmaceutically acceptable acid addition salts thereof having local anesthetic, beta-adrenergic blocking, antihypertensive and antiarrhythmic properties are disclosed. The compounds are prepared by reacting novel 1-aryloxy-4-chloro-2-butanols with amines. Methods for the preparation of the novel 1-aryloxy-4-chloro-2-butanol intermediates are also disclosed.

15 Claims, No Drawings

CERTAIN ARYLOXY-4-CHLORO-2-BUTANOL INTERMEDIATES

CROSS-REFERENCE TO RELATED APPLICATIONS

This application is a divisional of Ser. No. 06/418,940 filed 09-16-82, now abandoned, which is a divisional of Ser. No. 05/813,056, filed 07-05-77, now U.S. Pat. No. 4,379,167 issued 04-05-83; which in turn is a C-I-P of Ser. No. 05/730,498 filed 10-17-76, now abandoned which in turn is a C-I-P of Ser. No. 05/618,984 filed 10-02-75, now abandoned which in turn is a C-I-P of Ser. No. 05/518,122 filed 10-25-74, now abandoned.

BACKGROUND OF THE INVENTION

1. Field of the Invention

The present invention relates to certain organic compounds which may be referred to as disubstituted-2-butanols and is more particularly concerned with 1-aryloxy-4-amino-2-butanols and with processes for the production thereof, intermediate products useful in the preparation thereof and with processes for the preparation of such intermediates, compositions containing the 1-aryloxy-4-amino-2-butanols as active ingredients and methods for the use thereof.

2. Discussion of the Prior Art

The compounds which are the subject of this invention are related to known 1-aryloxy-3-amino-2-propanols as having beta-adrenergic blocking, anticonvulsant, sedative and tranquilizing activity. Among the United States patents disclosing the aforementioned 1,3-disubstituted-2-propanols and their pharmacological properties are U.S. Pat. Nos. 3,337,628; 3,415,873; 3,432,545 and 3,520,919. U.S. Pat. No. 3,337,628 in particular discloses 1-isopropyl-amino-3-(1-naphthyloxy)-2-propanol which compound is a potent beta-adrenergic blocking agent.

SUMMARY OF THE INVENTION

The present invention is especially concerned with novel 1-aryloxy-4-amino-2-butanols having the formula:

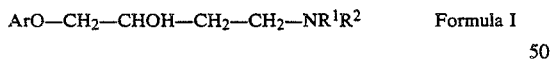

$$\text{ArO}-\text{CH}_2-\text{CHOH}-\text{CH}_2-\text{CH}_2-\text{NR}^1\text{R}^2 \quad \text{Formula I}$$

wherein;

Ar is 1-naphthyl, 2-naphthyl, indene-4(or 5-)yl, 3-(or 5-) chloro-2-pyridyl, phenyl, monosubstituted phenyl or disubstituted phenyl, $R^1$ is lower alkyl, phenyl, phenylalkyl, 2-hydroxymethyl-2-propyl, adamantyl or lower cycloalkyl, $R^2$ is hydrogen or lower alkyl, $R^1$ and $R^2$ together with the adjacent nitrogen form a heterocyclic residue, and pharmaceutically acceptable acid addition salts thereof.

The compounds of the invention having the foregoing Formula I are generally characterized by important and significant pharmacological activity, which is indicative of their use in counteracting certain physiological abnormalities in an animal body. The compounds possess local anesthetic, beta-adrenergic blocking, antihypertensive and antiarrhythmic properties.

The 1-aryloxy-4-amino-2-butanols were evaluated for pharmacological activity and were found to possess antiarrhythmic properties against experimentally induced cardiac arrhythmias in dogs. The prior art homolog 1,3-disubstituted-2-propanols also have antiarrhythmic activity. However, in contrast to the prior art 2-propanols, the novel 2-butanols of the present invention have minimal beta-adrenergic blocking activity, enabling them to be employed in controlling moderate to serious arrhythmias without the dangers of cardiac failure and respiratory difficulties, which dangers are attendant when the prior art 1,3-disubstituted-2-propanols having potent beta-adrenergic blocking activity are used in controlling cardiac arrhythmias.

Compounds of Formula I wherein Ar is 1-naphthyl and $-\text{NR}^1\text{R}^2$ is lower-alkylamino, lower cycloalkylamino wherein lower cycloalkyl has from 5 to 7 carbon atoms, phenylalkylamino, 2-hydroxymethyl-2-propylamino or phenylamino represent preferred compounds for their antiarrhythmic activity.

Compounds of Formula I wherein Ar is an ortho-lower-alkoxyphenoxy radical, particularly methoxy- and ethoxy-phenoxy radicals, and $-\text{NR}^1\text{R}^2$ is lower-alkylamino, lower cycloalkylamino wherein lower cycloalkyl has from 5 to 7 carbon atoms, phenylalkylamino, 2-hydroxymethyl-2-propylamino or phenylamino are also of particular interest for their antiarrhythmic activity.

To illustrate the utility of the compounds of this invention the following tabulation indicates the amount of certain representative compounds of this invention to correct ouabain-induced arrhythmias in anesthetized dogs.

TABLE 1

| Example | Average Corrective Dose (mg/kg, i.v.) | No. of Tests |
|---|---|---|
| 46 | 12.5 | 1 |
| 47 | 7.0 | 2 |
| 1 | 2.75 | 2 |
| 14 | 19.0 | 2 |
| 15 | 3.5 | 2 |
| 17 | 5.0 | 2 |
| 7 | 1.75 | 2 |
| 19 | 9.3 | 2 |
| 6 | 5.5 | 1 |
| 23 | 9.3 | 2 |
| 3 | 3.5 | 2 |
| 28 | 3.0 | 2 |
| 30 | 2.0 | 2 |
| 37 | 8.0 | 1 |
| 42 | 2.25 | 2 |
| 73 | 3.25 | 2 |
| 74 | 2.5 | 1 |
| 75 | 4.0 | 2 |

It is accordingly an object of this invention to provide novel 1-aryloxy-4-amino-2-butanols which are useful pharmacologically because of their aforesaid types of activity, processes for the production thereof, and intermediate products useful in the preparation thereof and processes for the production of such intermediates which in themselves have useful pharmacological activity. A further object is to provide novel compositions containing 1-aryloxy-4-amino-2-butanols as active ingredients and methods for their use. Other objects of the invention will be apparent to one skilled in the art, and still other objects will become apparent hereinafter.

In the definitions of the symbols in foregoing Formula I and where they appear elsewhere throughout this specification, the terms have the following significance.

The term "lower alkyl" as used herein includes straight and branched chain radicals of up to eight carbon atoms inclusive and is exemplified by such groups as methyl, ethyl, propyl, isopropyl, tertiary butyl, amyl, isoamyl, hexyl, heptyl, octyl, and the like.

The term "lower alkoxy" has the formula —O-lower alkyl.

When halogen is referred to herein, preferably but not necessarily, a halogen of atomic weight in excess of eighteen but not greater than eighty is employed.

The term "heterocyclic residue" as used herein includes basic saturated monocyclic heterocyclic radicals and basic unsaturated monocyclic heterocyclic radicals of less than twelve carbon atoms, as exemplified by piperidino; (lower alkyl) piperidino, e.g., 2-, 3-, or 4-(lower alkyl)piperidino; pyrrolidino; morpholino; di-(lower alkyl)morpholino, e.g., 3,5-dimethylmorpholino; 2,6-dimethylmorpholino; piperazino; (lower alkyl)-piperazino (e.g., $N^4$-methylpiperazino); phenyl-piperazino (e.g., $N^4$-phenylpiperazino); 1,2,3,4-tetrahydroisoquinolyl; 1,2,5,6-tetrahydropyridino, 4-(2-pyridyl)piperazino, and phthalimido.

Included in the term "phenylalkyl" are groups such as benzyl, phenethyl, methylbenzyl, phenpropyl, and the like.

The term "lower cycloalkyl" includes cyclic radicals having up to eight carbon atoms and includes radicals such as cyclopropyl, cyclobutyl, cyclopentyl, cyclohexyl, cycloheptyl and cyclooctyl.

The term "phenyl" includes the unsubstituted phenyl radical, the substituted phenyl radical and the disubstituted phenyl radical. Among the suitable substituted and disubstituted phenyl radicals are those which are substituted by any radical or radicals which are not reactive or otherwise interfering under the conditions of reaction in preparing the desired compound, such radicals including lower alkyl, lower alkoxy, trifluoromethyl, acetyl, acetylamino, halo, trifluoromethyl, and phenyl. The substituted phenyl radicals have preferably one or two substituents such as those given above and, furthermore, the substituents can be in various available positions of the phenyl nucleus and, when more than one substituent is present, can be the same or different and can be in various combinations relative to each other. The lower alkyl and lower alkoxy substituents each have preferably from one to four carbon atoms which can be arranged as straight or branched chains. A total of nine carbon atoms in all ring substituents, making a total of fifteen carbon atoms in the radical, is the preferred maximum.

The compounds of the invention are most conveniently employed in the form of pharmaceutically acceptable acid addition salts. Such salts have improved water solubility over the free bases. Appropriate acid addition salts are those derived from mineral acids such as hydrochloric, hydrobromic, sulfuric and phosphoric; and organic acids such as acetic, citric, lactic, maleic, oxalic, fumaric and tartaric. The preferred acid addition salt is the hydrochloride. The acid addition salts are conveniently prepared by reaction of the basic compounds with the selected acid, either or both of which may be in the form of ether, alcohol or acetone solutions.

The present invention also includes the novel 1-aryloxy-4-chloro-2-butanols of Formula IV which are useful as intermediates for preparing the final amine products of Formula I and they may be prepared by the process diagrammed in Chart I, wherein all of the symbols have the meanings given previously.

CHART I
PREPARATION OF STARTING
1-ARYLOXY-4-CHLORO-2-BUTANOLS (IV)

ArOH + ClCH$_2$—CHOH—CH$_2$—CH$_2$—Cl $\xrightarrow{OH^-}$

II          III

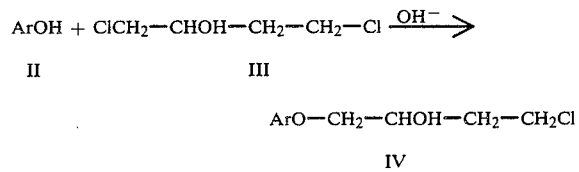

IV

The 1-aryloxy-4-chloro-2-butanols (IV) are generally prepared by treating an aqueous basic solution or an aqueous-alcoholic basic solution of a phenol, a substituted phenol or an aryl compound having an acidic hydroxyl group of Formula II with 1,4-dichloro-2-butanol III. The addition is carried out at or below 70° C., preferably at from about 30° C. to about 65° C. over a period of from about three hours to about eight hours. Subsequent to the addition the reaction mixture is heated at from about 50° C. to about 75° C., preferably at 60° C. to 70° C. for a period of from about six hours to about forty-eight hours, usually for a period of from twelve hours to eighteen hours. The 1-aryloxy-4-chloro-2-butanol is isolated from the reaction mixture by extraction using a suitable organic solvent as, for example, ether, isopropyl ether or chloroform, evaporation of the solvent after drying to give the 2-butanol which is isolated by suitable means such as distillation or crystallization. Alternatively, the 1-aryloxy-4-chloro-2-butanol can be prepared by adding an aqueous basic solution to a mixture of the phenol or the compound having an acidic hydroxyl group and 1,4-dichloro-2-butanol at a rate so as to maintain the reaction mixture at a pH of from about 9.0 to about 10.5, preferably at a pH of 9.5 to 10.0. The product is isolated as described hereinabove.

The following preparations are given by way of illustration only and are in no event to be construed as limiting.

Preparation 1

4-Chloro-1-phenoxy-2-butanol

To a mixture which contained 282 g. (3 moles) of phenol, one liter of water and 300 ml. of 50% sodium hydroxide was added slowly with stirring at 60° C. 443.36 g. (3.1 moles) of 1,4-dichlorobutanol. Stirring was continued at 60° C. for 16 hr. The resulting mixture was extracted twice with one liter of ether and the combined ether extracts were washed with water to neutrality and dried overnight over sodium sulfate. The dried ether mixture was concentrated to dryness under reduced pressure. The residue was distilled and yielded 435 g. of product which was collected at 135°–138° C./0.05 mm. The product solidified and was recrystallized using pet. ether (60°–110° C.) to give a white crystalline solid which melted at 52°–54° C.

Analysis: Calculated for $C_{10}H_{13}ClO_2$: C, 59.86; H, 6.53. Found: C, 59.72; H, 6.37.

Preparation 2

4-Chloro-1-(2-chlorophenoxy)-2-butanol.

To a mixture of 129 g. (1 mole) of 2-chlorophenol, 60 g. of potassium hydroxide, 100 ml. of water and 400 ml. of isopropanol was added 1.3 moles (185.9 g.) of 1,4-dichloro-2-butanol with stirring at 50° C. The resulting mixture was heated in a steam bath at 65° C. overnight and extracted with 300 ml. of isopropyl ether. The ether extract was washed successively with 1N sodium hydroxide, water and dried over sodium sulfate. The dried ether solution was concentrated and the oily residue was distilled under reduced pressure yielding 152 g. of an oily substance (b.p. 130°–131° C./0.01 mm.).

Analysis: Calculated for $C_{10}H_{15}ClO_2$: C, 51.08; H, 5.15. Found: C, 51.13; H, 5.14.

Preparation 3

4-Chloro-1-(3,5-dimethylphenoxy)-2-butanol

To a mixture of 245 g. (2 moles) of 3,5-dimethylphenol and 2 liters of 2N sodium hydroxide was added 2.5 moles of 1,4-dichlorobutanol with stirring at 65° C. overnight. The solid precipitate which separated on cooling was filtered and washed with water to neutrality. Recrystallization with isopropyl ether yielded 375 g. of white crystalline solid which melted at 74°–76° C.

Analysis: Calculated for $C_{12}H_{17}ClO_2$: C, 62.02; H, 7.49. Found: C, 63.96; H, 7.66.

Preparation 4

4-Chloro-1-(4-chloro-3-methylphenoxy)-2-butanol

To a mixture of 286 g. (2 moles) of 3-methyl-4-chlorophenol, 700 ml. of tertiary butanol, 700 ml. of water and 3.0 moles of 1,4-dichloro-2-butanol, sodium hydroxide (2.9 moles, 230 g. in 700 ml. water) was added with stirring at 40° C. to maintain a pH of 9.5–10.0 as the reaction progressed. The addition was 10 hr.; the reaction was stirred at 40° C. for 48 hr. The resulting reaction mixture was extracted with chloroform sodium hydroxide at 25° C. The chloroform extract was washed with sodium sulfate. The dried chloroform solution was concentrated and the residue was distilled under reduced pressure to give 110.9 g. of the product which distilled at 135°–143° C./0.007 mm. and melted at 87°–89° C. after recrystallization with isopropanol and pet. ether (30.60°).

Analysis: Calculated for $C_{11}H_{14}Cl_2O_2$: C, 53.03; H, 5.66. Found: C, 53.11; H, 5.61.

Preparation 5

4-Chloro-1-(4-chloro-2-methylphenoxy)-2-butanol

4-Chloro-1-(4-chloro-2-methylphenoxy)-2-butanol was prepared according to the procedure of Preparation 4 using 105 g. (0.74 mole) of 2-methyl-4-chlorophenol, 171.5 g. (1.2 mole) of 1,4-dichloro-2-butanol, 50.3 g. of sodium hydroxide, 300 ml. of water and 300 ml. of tertiary butanol. There was obtained 84 g. (45.5%) of product which distilled at 135° C./0.01 mm.

Analysis: Calculated for $C_{11}H_{14}O_2Cl_2$: C, 53.03; H, 5.66. Found: C, 53.41; H, 5.70.

Preparation 6

4-Chloro-1-(naphthyloxy)-2-butanol

To a mixture of 1 mole (147 g.) of 1-naphthol, 350 ml. of water and 2 moles (112 g.) of potassium hydroxide was added at 54° C. 1 mole (143 g.) of 1,4-dichloro-2-butanol. The temperature of the reaction mixture was kept below 60° C. during the addition of the chlorobutanol. The reaction mixture was heated at 65° C. for 12 hr., then mixed with 500 ml. of water and 350 ml. of chloroform. The chloroform layer was separated, washed with water, dried over sodium sulfate, concentrated and the residual oil distilled under reduced pressure to give 128 g. of a crystalline solid which was distilled at 162°–165° C./0.01 mm. The solid was recrystallized with ether and pet. ether (30°–60°) to give material melting at 75°–77° C.

Analysis: Calculated for $C_{14}H_{15}O_2Cl$: C, 67.07; H, 6.03. Found: C, 67.19; H, 6.19.

Preparation 7

4-Chloro-(4-biphenylyloxy)-2-butanol

To a solution of 1 mole (158 g.) of 4-phenylphenol 100 g. of sodium hydroxide and 500 ml. of water was added 1 mole (143.02 g.) of 1,4-dichloro-2-butanol with stirring at 40° C. The resulting mixture was heated at 68° C. in a steam bath for 6 hr., cooled and extracted with 300 ml. of chloroform. The chloroform extract was washed with water to neutrality, dried over sodium sulfate and concentrated to dryness. The solid residue was recrystallized with isopropanol and yielded 180 g. of a white crystalline solid which melted at 123°–124° C.

Analysis: Calculated for $C_{16}H_{17}ClO_2$: C, 69.44; H, 6.19. Found: C, 69.79; H, 6.22.

Preparation 8

4-Chloro-1-(3-trifluoromethylphenoxy)-2-butanol

To a mixture of 0.5 mole (75 g.) of m-trifluoromethylphenol, 1 mole (56 g.) of potassium hydroxide, 100 ml. of water and 400 ml. of isopropanol was added 0.6 mole (84 g.) of 1,4-dichloro-2-butanol with stirring at temperature below 55° C. The resulting reaction mixture was heated at 65° C. for 20 hr., mixed with 2 liters of water, and extracted with 400 ml. of isopropyl ether. The ether extract was washed with 0.5N sodium hydroxide and then with water, dried over sodium sulfate and distilled under reduced pressure. The distillate which was collected at 120°–124° C./0.01 mm. solidified at room temperature and melted at 50°–52° C.

Analysis: Calculated for $C_{11}H_{12}ClF_3O_2$: C, 49.18; H, 4.50. Found: C, 49.35; H, 4.47.

Preparation 9

4-Chloro-1-(4-chlorophenoxy)-2-butanol

4-Chloro-1-(4-chlorophenoxy)-2-butanol was prepared using the procedure of Preparation 7 from 45 g. (0.5 mole) of p-chlorophenol, 72 g. (0.5 mole) of 1,4-dichloro-2-butanol, 40 g. (1.0 mole) of sodium hydroxide and 400 ml. of water to give 85 g. (36.1%) of product which melted at 62°–64° C. after recrystallization from isopropanol.

Analysis: Calculated for $C_{10}H_{15}ClO_2$: C, 51.09; H, 5.14. Found: C, 51.76; H, 5.12.

Preparation 10

4-Chloro-1-(2-methoxyphenoxy)-2-butanol

To a mixture of 2 moles (248.26 g.) of 2-methoxyphenol, 4 moles (160 g.) of sodium hydroxide, 250 ml. of water and 1 liter of isopropanol was added with stirring 2.2 moles (314.64 g.) of 1,4-dichloro-2-butanol. The mixture was refluxed gently overnight. The reaction mixture was extracted with 1 liter of isopropyl ether, dried over sodium sulfate and distilled under reduced pressure. The distillate which was collected at 136°–138° C./0.015 mm. (396.8 g.) solidified to a white crystalline solid which melted at 48°–50° C.

Analysis: Calculated for $C_{11}H_{14}O_3Cl$: C, 57.52; H, 6.14. Found: C, 57.49; H, 6.54.

Using the procedures disclosed in Preparations 1–10, starting from the appropriate phenol II and 1,4-dichloro-2-butanol III, various other 1-aryloxy-4-chloro-2-butanols IV are prepared.

Preparation 11

4-Chloro-1-(2-methyl-5-chlorophenoxy)-2-butanol, b.p. 135°–8° C./0.05 mm. was prepared from 2-methyl-5-chlorophenol and 1,4-dichloro-2-butanol.

Preparation 12

4-Chloro-1-(2-naphthyloxy)-2-butanol, m.p. 101°–102° C., was prepared from 2-naphthol and 1,4-dichloro-2-butanol.

Preparation 13

4-Chloro-1-(4-acetylaminophenoxy)-2-butanol, m.p. 125°–128° C., was prepared from 4-acetylaminophenol and 1,4-dichloro-2-butanol.

Preparation 14

4-Chloro-1-(4-methoxyphenoxy)-2-butanol, m.p. 61°–63° C., was prepared from 4-methoxyphenol and 1,4-dichloro-2-butanol.

Preparation 15

4-Chloro-1-(3-chloro-2-pyridyloxy)-2-butanol, m.p. 56°–58° C., was prepared from 3-chloro-2-hydroxypyridine and 1,4-dichloro-2-butanol.

Preparation 16

4-Chloro-1-(5-chloro-2-pyridyloxy)-2-butanol, was prepared from 5-chloro-2-hydroxypyridine and 1,4-dichloro-2-butanol.

Preparation 17

4-Chloro-1-(inden-5-yloxy)-2-butanol, m.p. 56°–58° C., was prepared from 6-hydroxyindene and 1,4-dichloro-2-butanol.

Preparation 18

4-Chloro-1-(3-chlorophenoxy)-2-butanol, 60°–62° C., was prepared from 3-chlorophenol and 1,4-dichloro-2-butanol.

Preparation 19

4-Chloro-1-(2-ethoxyphenoxy)-2-butanol, b.p. 130°–132° C./0.01 mm. was prepared from 2-ethoxyphenol and 1,4-dichloro-2-butanol.

Preparation 20

4-Chloro-1-(4-acetylphenoxy)-2-butanol, m.p. 125°–128° C., was prepared from 4-acetylphenol and 1,4-dichloro-2-butanol.

Preparation 21

4-Chloro-1-(o-phenylphenoxy)-2-butanol, b.p. 156°–160° C./0.25 mm., was prepared from o-phenylphenol and 1,4-dichloro-2-butanol.

The preparation of the novel 1-aryloxy-4-amino-2-butanols I of the present invention is designated in the following reaction sequence:

CHART 2
PREPARATION OF
1-ARYLOXY-4-AMINO-2-BUTANOLS

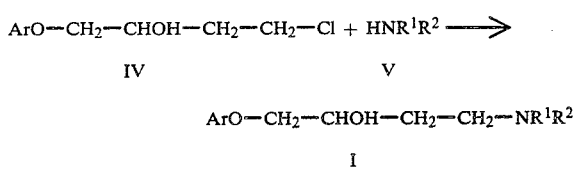

wherein all of the symbols have the meanings given hereinabove.

In the reaction sequence the 1-aryloxy-4-chloro-2-butanol (IV) is reacted with an amine (V) to give the novel 1-aryloxy-4-amino-2-butanols (I). The foregoing reaction can be carried out by (A) heating a mixture of the chloro compound and the amine with a solvent in a steel bomb, (B) heating a mixture of the chloro compound and the amine without a solvent in a steel bomb, (C) refluxing a mixture of the chloro compound, the amine and a solvent at atmospheric pressure or (D) heating a mixture of the chloro compound and the amine without a solvent at atmospheric pressure and at a suitable temperature. The selected procedure is somewhat dependent on the nature of the amine reactant. Thus, when the amine is a low molecular volatile amine process A or B is preferred and the bomb contents are heated at from about 100° C. to about 150° C. for a period of from about 12 hours to about 24 hours. When the amine is a high molecular weight non-volatile amine or an amine having low volatility, process C or D is preferred and the reaction mixture is refluxed at the temperature of the solvent used or the mixture is heated at from about 100° C. to about 150° C. The reaction time can be varied, reaction times being somewhat shorter when the chloro compound and the amine are reacted together in the absence of a solvent and a higher reaction temperature is employed. The reaction product in each case is isolated by conventional acid-base extraction procedures and the free base, if desired, is converted to a pharmaceutically acceptable acid addition salt which is further purified by crystallization from a suitable solvent or solvent system. 1-Aryloxy-4-amino-2-butanols which do not form well defined salts can be purified by vacuum distillation.

Examples 1-6 illustrate the preparation of the novel 1-aryloxy-4-amino-2-butanol compounds of the present invention by one of the four optional processes. Table I summarizes the physical data of additional compounds within the scope of Formula I and indicates the process used to prepare each compound.

Table II contains the analytical data of the compounds listed in Table I.

EXAMPLE 1

4-Isopropylamino-1-(1-naphthyloxy)-2-butanol Hydrochloride

A mixture of 27.1 g. (0.1 mole) of 1-(1-naphthyloxy)-2-hydroxybutyl chloride and 100 ml. of isopropylamine in a steel bomb was heated at 120° C. for 24 hours. The reaction mixture was mixed with 300 ml. of 6N hydrochloric acid and extracted with ether at room temperature. The acidic aqueous solution was made basic, extracted with isopropyl ether, dried over sodium sulfate, then concentrated to dryness. The residue was dissolved in isopropanol and mixed with ethereal hydrogen chloride. The white crystalline precipitate was recrystallized from isopropanol and isopropyl ether to give hydrochloride salt which melted at 126°-128° C.

Analysis: Calculated for $C_{17}H_{24}ClNO_2$: C, 65.90; H, 7.81; N, 4.52. Found: C, 65.67; H, 7.91; N, 4.34.

EXAMPLE 2

4-(1,2,3,4-Tetrahydroisoquinolin-2-yl)-1-(1-naphthyloxy)-2-butanol Hydrochloride A mixture of 12.5 g. (0.05 mole) of 1-(1-naphthyloxy)-2-hydroxybutyl chloride, 9.97 g. (0.075 mole) of 1,2,3,4-tetrahydroisoquinoline and 300 ml. of isopropanol was refluxed for 15 hr. On standing at room temperature a crystalline precipitate formed. The mixture was filtered and the filtrate concentrated to dryness under reduced pressure. The semi-solid residue which crystallized was recrystallized from acetone. The 12.2 g. of crystalline solid material melted at 169°-171° C.

Analysis: Calculated for $C_{23}H_{26}ClNO_2$: C, 71.96; H, 6.83; N, 3.65. Found: C, 71.69; H, 6.76; N, 3.60.

EXAMPLE 3

1-(1-Naphthyloxy)-4-phenethylamino-2-butanol Hydrochloride

A mixture of 12.5 g. (0.05 mole) of 1-(1-naphthyloxy)-2-hydroxybutyl chloride and 14.5 g. (0.1 mole) of phenethylamine was heated at 120° C. for 20 min. on a hot plate. The resulting mixture was mixed with 250 ml. of acetone, heated to boiling and then filtered at room temperature. The filtrate was treated with 50 ml. of ethereal hydrogen chloride. The resulting white precipitate was filtered. The white crystalline solid was recrystallized from acetone and yielded 11.8 g. of the hydrochloride salt which melted at 163°-165° C.

Analysis: Calculated for $C_{22}H_{26}NO_2Cl$: C, 71.05; H, 7.05; N, 3.77. Found: C, 70.99; H, 6.98; N, 3.61.

EXAMPLE 4

1-(2-Chlorophenoxy)-4-(1,2,3,4-tetrahydroisoquinolyl)-2-butanol Hydrochloride Hydrate A mixture of 11.8 g. (0.05 mole) of 1-(2-chlorophenoxy)-2-hydroxybutyl chloride, 13.3 g. (0.1 mole) of 1,2,3,4-tetrahydroisoquinoline and 100 ml. of n-butanol was heated in a steel bomb at 120° C. for 24 hr. The reaction mixture was filtered at room temperature, the filtrate was mixed with 200 ml. 3N hydrochloric acid and extracted twice with 100 ml. isopropyl ether. The aqueous acidic solution was made basic and extracted with isopropyl ether and treated with ethereal hydrogen chloride. Recrystallization with isopropanol yielded 6 g. of the hydrochloride hydrate of the product which melted at 118°-120° C.

Analysis: Calculated for $C_{19}H_{25}Cl_2NO_3$: C, 59.07; H, 6.52; N, 3.63. Found: C, 59.08; H, 6.51; N, 3.55.

EXAMPLE 5

4-(Isopropylamino)-1-(o-methoxyphenoxy)-2-butanol Hydrochloride

A mixture which contained 11.6 g. (0.05 mole) of 1-(2-methoxyphenoxy)-2-hydroxybutyl chloride, 50 ml. of isopropyl amine and 100 ml. of n-butanol was charged in a steel bomb and heated at 120° C. for 24 hr. The resulting reaction mixture was filtered. The filtrate was concentrated to dryness and mixed with 200 ml. of 3N hydrochloric acid, extracted with ether and the aqueous layer was made basic. The base insoluble oil was extracted into isopropyl ether, dried over sodium sulfate and concentrated to dryness. The residue was dissolved in isopropanol and mixed with 20 ml. ethereal hydrogen chloride. The gummy precipitate recrystallized using isopropyl ether and isopropanol. The hydrochloride (8.3 g.) melted at 83°-85° C.

Analysis: Calculated for $C_{14}H_{24}ClNO_3$: C, 58.02; H, 8.35; N, 4.83. Found: C, 57.44; H, 8.31; N, 4.72.

EXAMPLE 6

1-(o-Chlorophenoxy)-4-(4-phenyl-1-piperazinyl)-2-butanol

A mixture of 35.1 g. (0.15 mole) of 1-(o-chlorophenoxy)-2-hydroxybutyl chloride, 32.6 g. (0.2 mole) of N-phenylpiperazine and 400 ml. of isopropanol was refluxed for 48 hr. The reaction mixture was allowed to stand in a refrigerator overnight and filtered. The filtrate was treated with ethereal hydrogen chloride and the salt precipitated by the addition of ether. The white crystalline solid which formed was dissolved in 0.1 mole of hydrochloric acid and then neutralized with sodium hydroxide producing a crystalline precipitate. This was recrystallized with isopropanol yielding 36 g. of the free base of the product which melted at 100°–101.5° C.

Analysis: Calculated for $C_{20}H_{25}N_2O_2Cl$: C, 66.56; H, 6.98; N, 7.76. Found: C, 66.49; H, 7.03; N, 7.86.

The physical constants of some representative 1-aryloxy-4-amino-2-butanols made from 1-aryloxy-4-chloro-2-butanols and a selected amine by processes A, B, C and D are shown in Table I and Table II.

TABLE II

Examples 7 through 75

$$Ar-O-CH_2-\underset{\underset{OH}{|}}{CH}-CH_2-CH_2-N\underset{R^2}{\overset{R^1}{\diagup}}$$

| Example Number | Ar | $-N\underset{R^2}{\overset{R^1}{\diagup}}$ | Salt | M.P. °C. | Process |
|---|---|---|---|---|---|
| 7 | 1-$C_{10}H_7$ | —$NHC_2H_5$ | HCl | 153–5 | A |
| 8 | 1-$C_{10}H_7$ | —$NHC_6H_{11}$ | HCl | 158–60 | D |
| 9 | 1-$C_{10}H_7$ | —$NOC_4H_8{}^a$ | — | 54–6 | D |
| 10 | 1-$C_{10}H_7$ | —$NOC_4H_6(CH_3)_2{}^b$ | $HCl.H_2O$ | 118–20 | D |
| 11 | 1-$C_{10}H_7$ | —$N(CH_3)C_6H_{11}$ | — | 62–5 | D |
| 12 | 1-$C_{10}H_7$ | —$NC_5H_{10}{}^c$ | HCl | 135–7 | D |
| 13 | 1-$C_{10}H_7$ | —$NHCH_2C_6H_5$ | $HCl.H_2O$ | 83–5 | D |
| 14 | 4-$C_6H_5$—$C_6H_4$ | —$NHCH(CH_3)_2$ | HCl | 190–2 | B |
| 15 | 3-$CH_3$—4-$ClC_6H_3$ | —$NHCH(CH_3)_2$ | — | 74–6 | A |
| 16 | 3-$CF_3C_6H_4$ | —$NHCH(CH_3)_2$ | HCl | 92–4 | B |
| 17 | 2-$CH_3$—5-$ClC_6H_3$ | —$N(CH_3)CH_2C_6H_5$ | HCl | 169–71 | C |
| 18 | 3-$CH_3$—4-$ClC_6H_3$ | —$NH(CH_2)_2C_6H_5$ | HCl | 163–5 | A |
| 19 | 2-$CH_3$—4-$ClC_6H_3$ | —$NH(CH_2)_2C_6H_5$ | HCl | 128–30 | A |
| 20 | 2-$ClC_6H_4$ | —$NHC(CH_3)_2CH_2OH$ | HCl | 117–119 | C |
| 21 | $C_6H_5$ | —$NH(CH_2)_2C_6H_5$ | HCl | 143–4 | D |
| 22 | 2-$CH_3$—4-$ClC_6H_3$ | —$NC_5H_9$—4-$C_6H_5$ | HCl | 148–50 | D |
| 23 | 2-$CH_3$—4-$ClC_6H_3$ | —$NC_4H_8N$—$C_6H_5{}^e$ | di-HCl | 186–8 | C |
| 24 | 2-$ClC_6H_4$ | —$NC_5H_{10}{}^c$ | HCl | 159–60 | C |
| 25 | 3-$CF_3C_6H_4$ | —$NH(CH_2)_2C_6H_5$ | HCl | 131–3 | D |
| 26 | 2-$CH_3$—5-$ClC_6H_4$ | —$NH(CH_2)_2C_6H_5$ | HCl | 141–3 | D |
| 27 | 3-$ClC_6H_4$ | —$NH(CH_2)_2C_6H_5$ | HCl | 154–6 | D |
| 28 | 2-$CH_3OC_6H_4$ | —$NH(CH_2)_2C_6H_5$ | — | 112–14 | D |
| 29 | $C_6H_5$ | —$NHCH_2C_6H_5$ | $HCl.\tfrac{1}{2}H_2O$ | 108–10 | D |
| 30 | 2-$CH_3OC_6H_4$ | —$NHC_6H_{11}$ | $H_2O$ | 55–7 | C |
| 31 | 3-$ClC_6H_4$ | —$NHCH_2C_6H_5$ | HCl | 139–41 | D |
| 32 | 2-$CH_3$—4-$ClC_6H_3$ | —$NC_9H_{10}{}^f$ | HCl | 149–51 | D |
| 33 | 3,5-$CH_3C_6H_3$ | —$NH(CH_2)_2C_6H_5$ | $HCl.\tfrac{1}{2}H_2O$ | 117–20 | D |
| 34 | 3,5-$CH_3C_6H_3$ | —$NC_4H_8N$—$C_6H_5$ | — | 88–90 | D |
| 35 | 3,5-$CH_3C_6H_3$ | —$NC_9H_{10}{}^f$ | $HCl.\tfrac{1}{2}H_2O$ | 141–3 | D |
| 36 | 3,5-$CH_3C_6H_3$ | —$NC_5H_7$—4-$C_6H_5{}^g$ | HCl | 162–4 | D |
| 37 | 3,5-$CH_3C_6H_3$ | —$N(CH_3)C_6H_{11}$ | HCl | 158–60 | D |
| 38 | 2-$ClC_6H_4$ | —$NH(CH_2)_2C_6H_5$ | — | 92–4 | D |
| 39 | $C_6H_5$ | —$NC_4H_8N$—2-$C_5H_4N^h$ | di-maleate | 123–5 | D |
| 40 | $C_6H_5$ | —$N(CH_3)C_6H_{11}$ | — | 50–2 | D |
| 41 | $C_6H_5$ | —$N(CH_3)CH_2C_6H_5$ | maleate | 118–20 | D |
| 42 | 2-$CH_3OC_6H_4$ | —$N(CH_3)C_6H_{11}$ | maleate | 109–11 | D |
| 43 | 2-$CH_3OC_6H_4$ | —$NOC_4H_6(CH_3)_2$ | — | — | D |
| 44 | 2-$CH_3OC_6H_4$ | —$NC_4H_8N$—2-$C_5H_4N^h$ | $3HCl.\tfrac{1}{2}H_2O$ | 95–7 | D |
| 45 | 2-$CH_3OC_6H_4$ | —$NHC_5H_9{}^i$ | HCl | 112–14 | D |
| 46 | 2-$C_{10}H_7$ | —$NC_5H_7$—4-$C_6H_5{}^g$ | HCl | 168–70 | C |
| 47 | 2-$C_{10}H_7$ | —$NHCH(CH_3)_2$ | — | 96–98 | B |
| 48 | 4-$CH_3OC_6H_4$ | —$N(CH_3)C_6H_{11}$ | — | 50–2 | C |
| 49 | 4-$CH_3CONHC_6H_4$ | —$NHC_6H_{11}$ | — | 140–2 | C |
| 50 | 4-$CH_3COC_6H_4$ | —$NHC_6H_{11}$ | — | 93–5 | C |
| 51 | 1-$C_{10}H_7$ | —$NHC(CH_3)_2CH_2OH$ | — | 98–100 | C |
| 52 | 3,5-$CH_3C_6H_3$ | —$NHC_{10}H_{15}{}^j$ | HCl | 229–31 | C |
| 53 | 5-$C_9H_7{}^k$ | —$NHC_6H_{11}$ | — | 95–7 | C |
| 54 | 5-$C_9H_7$ | —$NHCH(CH_3)_2$ | $HCl.H_2O$ | 103–5 | C |
| 55 | 2-$CH_3$—5-$ClC_6H_3$ | —$NHC_6H_{11}$ | HCl | 189–92 | C |
| 56 | 4-$CH_3OC_6H_4$ | —$NHC_{10}H_{15}{}^j$ | — | 78–80 | C |
| 57 | 1-$C_{10}H_7$ | —$NHC_{10}H_{15}{}^j$ | HCl | 195–7 | C |
| 58 | 1-$C_{10}H_7$ | —$N(CH_3)C_8H_{15}$ | HCl | 143–5 | C |
| 59 | 4-$CH_3OC_6H_4$ | —$NHCH(CH_3)_2$ | HCl | 118–20 | C |
| 60 | 4-$CH_3OC_6H_4$ | —$NHC_6H_{11}$ | HCl | 136–8 | C |
| 61 | 5-$C_9H_7{}^k$ | —$NHC(CH_3)_2CH_2OH$ | — | 93–5 | C |
| 62 | 5-$ClC_5H_3N^l$ | —$NHC_6H_{11}$ | $HCl.H_2O$ | — | C |
| 63 | 1-$C_{10}H_7$ | —$N(CH_3)CH_2CH_2OH$ | HCl | 115–17 | C |
| 64 | 1-$C_{10}H_7$ | —$NHC_5H_9$ | HCl | 148–50 | D |
| 65 | 5-$ClC_5H_3N^l$ | —$NHCH(CH_3)_2$ | $2HCl.H_2O$ | 174–77 | C |
| 66 | 4-$C_6H_5$—$C_6H_4$ | —$NHC(CH_3)_2CH_2OH$ | HCl | 155–57 | C |
| 67 | 2-$C_2H_5OC_6H_4$ | —$NHCH_2C_6H_5$ | HCl | 107–7 | C |

TABLE II-continued
Examples 7 through 75

$$Ar-O-CH_2-\underset{\underset{OH}{|}}{CH}-CH_2-CH_2-N\overset{R^1}{\underset{R^2}{\diagdown}}$$

| Example Number | Ar | $-N\overset{R^1}{\underset{R^2}{\diagdown}}$ | Salt | M.P. °C. | Process |
|---|---|---|---|---|---|
| 68 | $2\text{-}C_2H_5OC_6H_4$ | $-NHC_6H_{11}$ | — | 83–5 | C |
| 69 | $2\text{-}C_2H_5OC_6H_4$ | $-NC_9H_{16}{}^m$ | HCl | 140–2 | C |
| 70 | $2\text{-}C_2H_5OC_6H_4$ | $-NOC_4H_6(CH_3)_2{}^n$ | HCl | 115–17 | D |
| 71 | $1\text{-}C_{10}H_7$ | $-NHC_5H_9\text{-}2\text{-}CH_3$ | HCl | 176–8 | C |
| 72 | $1\text{-}C_{10}H_7$ | $-NHC_6H_{11}$ | — | 96–8 | C |
| 73 | $2\text{-}ClC_6H_4$ | $-NHCH(CH_3)_2$ | HCl | 88–90 | B |
| 74 | $3,5\text{-}CH_3C_6H_3$ | $-NHCH(CH_3)_2$ | — | 69.71 | B |
| 75 | $2\text{-}CH_3\text{-}4\text{-}ClC_6H_3$ | $-NHCH(CH_3)_2$ | HCl | 122–124 | B |

[a] morpholino
[b] 3,5-dimethylmorpholinyl
[c] piperidino
[d] 4-phenylpiperidino
[e] 4-phenylpiperazino
[f] 1,2,3,4-tetrahydroisoquinolyl
[g] 4-phenyl-1,2,3,6-tetrahydro-1-pyridino
[h] 4-(2-pyridyl)piperazino
[i] cyclopentylamino
[j] 1-adamantylamino
[k] inden-5-yl
[l] 5-chloro-2-pyridyl
[m] 1-decahydroquinoline
[n] 1-(2,6-dimethyl)morpholino.

TABLE III
Analytical Data on Examples 7 through 75

| Example Number | Emperical Formula | Calculated C | Calculated H | Calculated N | Found C | Found H | Found N |
|---|---|---|---|---|---|---|---|
| 7 | $C_{16}H_{23}ClNO_2$ | 64.75 | 7.81 | 4.72 | 63.97 | 7.52 | 4.51 |
| 8 | $C_{20}H_{28}ClNO_2$ | 68.65 | 8.07 | 4.00 | 68.46 | 8.16 | 4.03 |
| 9 | $C_{18}H_{23}NO_3$ | 71.73 | 7.69 | 4.65 | 71.59 | 7.70 | 4.58 |
| 10 | $C_{20}H_{30}ClNO_4$ | 62.57 | 7.88 | 3.65 | 62.51 | 7.68 | 3.73 |
| 11 | $C_{21}H_{29}NO_2$ | 77.02 | 8.93 | 4.28 | 76.89 | 8.95 | 4.17 |
| 12 | $C_{19}H_{26}ClNO_2$ | 67.95 | 7.80 | 4.17 | 67.73 | 7.79 | 4.06 |
| 13 | $C_{21}H_{26}ClNO_3$ | 67.10 | 6.97 | 3.73 | 67.33 | 6.89 | 3.88 |
| 14 | $C_{19}H_{26}ClNO_2$ | 67.94 | 7.80 | 4.17 | 67.90 | 7.78 | 3.72 |
| 15 | $C_{14}H_{22}ClNO_2$ | 61.87 | 8.16 | 5.15 | 61.13 | 8.05 | 4.99 |
| 16 | $C_{14}H_{21}NO_2F_3Cl$ | 51.30 | 6.46 | 4.27 | 51.24 | 6.42 | 4.41 |
| 17 | $C_{19}H_{25}Cl_2NO_2$ | 61.62 | 6.80 | 3.78 | 61.42 | 6.77 | 3.88 |
| 18 | $C_{19}H_{29}Cl_2NO_2$ | 61.62 | 6.80 | 3.78 | 61.51 | 6.89 | 3.88 |
| 19 | $C_{19}H_{25}Cl_2NO_2$ | 61.62 | 6.80 | 3.78 | 61.56 | 6.68 | 3.83 |
| 20 | $C_{14}H_{23}NO_3Cl_2$ | 51.86 | 7.15 | 4.32 | 51.85 | 7.17 | 4.40 |
| 21 | $C_{18}H_{24}NO_2Cl$ | 67.17 | 7.52 | 4.35 | 67.22 | 7.56 | 4.31 |
| 22 | $C_{22}H_{29}Cl_2NO_2$ | 64.39 | 7.12 | 3.41 | 64.10 | 7.28 | 3.57 |
| 23 | $C_{21}H_{29}Cl_3N_2O_2$ | 56.32 | 6.53 | 6.25 | 56.07 | 6.47 | 6.24 |
| 24 | $C_{15}H_{23}Cl_2NO_2$ | 56.26 | 7.24 | 4.37 | 56.00 | 7.23 | 4.30 |
| 25 | $C_{19}H_{23}ClF_3NO_2$ | 58.54 | 5.95 | 3.59 | 58.35 | 6.00 | 3.75 |
| 26 | $C_{19}H_{25}Cl_2NO_2$ | 61.62 | 6.80 | 3.78 | 61.61 | 6.85 | 3.64 |
| 27 | $C_{18}H_{23}Cl_2NO_2$ | 60.68 | 6.51 | 3.93 | 60.75 | 6.58 | 3.96 |
| 28 | $C_{19}H_{25}N_1O_3$ | 72.35 | 7.79 | 4.44 | 72.23 | 7.99 | 4.39 |
| 29 | $C_{34}H_{46}O_5Cl_2N_2$ | 64.45 | 7.32 | 4.42 | 64.75 | 7.19 | 4.66 |
| 30 | $C_{17}H_{29}NO_4$ | 65.57 | 9.38 | 4.50 | 65.53 | 8.86 | 4.46 |
| 31 | $C_{17}H_{21}Cl_2NO_2$ | 59.67 | 6.18 | 4.09 | 59.62 | 6.23 | 4.11 |
| 32 | $C_{20}H_{25}Cl_2NO_2$ | 62.83 | 6.59 | 3.66 | 62.52 | 6.60 | 3.31 |
| 33 | $C_{40}H_{58}Cl_2N_2O_5$ | 66.93 | 8.14 | 3.90 | 67.19 | 8.03 | 3.76 |
| 34 | $C_{22}H_{30}N_2O_2$ | 74.54 | 8.53 | 7.90 | 74.36 | 8.61 | 8.03 |
| 35 | $C_{44}H_{58}Cl_2N_2O_5$ | 69.00 | 7.63 | 3.66 | 68.59 | 7.72 | 3.70 |
| 36 | $C_{23}H_{30}NO_2Cl$ | 71.21 | 7.79 | 3.61 | 71.26 | 7.88 | 3.42 |
| 37 | $C_{19}H_{32}NO_2Cl$ | 66.74 | 9.43 | 4.10 | 66.72 | 9.46 | 3.98 |
| 38 | $C_{18}H_{22}N_1O_2Cl_1$ | 67.60 | 6.93 | 4.38 | 67.28 | 6.96 | 4.37 |
| 39 | $C_{27}H_{33}N_3O_{10}$ | 57.96 | 5.94 | 7.51 | 57.71 | 5.82 | 7.30 |
| 40 | $C_{17}H_{27}NO_2$ | 73.61 | 9.81 | 5.05 | 73.32 | 9.64 | 4.94 |
| 41 | $C_{22}H_{27}NO_6$ | 65.82 | 6.78 | 3.49 | 65.84 | 6.77 | 3.42 |
| 42 | $C_{22}H_{33}NO_7$ | 62.39 | 7.85 | 3.31 | 62.15 | 7.68 | 3.15 |
| 43 | $C_{17}H_{27}NO_4$ | 65.99 | 8.80 | 4.53 | 65.15 | 8.77 | 4.33 |
| 44 | $C_{20}H_{35}Cl_3N_3O_4$ | 49.24 | 7.23 | 8.61 | 49.18 | 6.99 | 8.85 |
| 45 | $C_{16}H_{26}ClNO_3$ | 60.85 | 8.30 | 4.43 | 60.71 | 8.12 | 4.34 |
| 46 | $C_{25}H_{28}ClNO_2$ | 73.25 | 6.88 | 3.42 | 72.59 | 6.99 | 3.43 |
| 47 | $C_{17}H_{23}NO_2$ | 74.69 | 8.48 | 5.12 | 74.21 | 8.50 | 5.02 |
| 48 | $C_{18}H_{29}NO_3$ | 70.32 | 9.51 | 4.56 | 70.15 | 9.41 | 4.56 |
| 49 | $C_{18}H_{28}N_2O_3$ | 67.47 | 8.81 | 8.74 | 67.35 | 8.75 | 8.65 |
| 50 | $C_{18}H_{27}NO_3$ | 70.79 | 8.91 | 4.59 | 70.71 | 8.91 | 4.76 |
| 51 | $C_{18}H_{25}NO_3$ | 71.26 | 8.30 | 4.62 | 71.34 | 8.23 | 4.46 |
| 52 | $C_{22}H_{34}ClNO_2$ | 69.54 | 9.02 | 3.69 | 69.26 | 8.95 | 3.73 |
| 53 | $C_{19}H_{29}NO_2$ | 75.21 | 9.63 | 4.62 | 75.04 | 9.55 | 4.60 |
| 54 | $C_{16}H_{28}ClNO_3$ | 60.46 | 8.88 | 4.41 | 59.81 | 8.05 | 4.47 |
| 55 | $C_{17}H_{26}ClNO_2$ | 58.79 | 7.55 | 4.03 | 58.54 | 7.70 | 3.93 |
| 56 | $C_{21}H_{32}NO_4$ | 69.58 | 8.90 | 3.86 | 69.29 | 8.89 | 4.20 |
| 57 | $C_{24}H_{35}ClNO_4$ | 65.96 | 8.07 | 3.20 | 66.31 | 7.85 | 3.25 |
| 58 | $C_{23}H_{34}ClNO_2$ | 70.48 | 8.73 | 3.57 | 69.98 | 8.64 | 3.45 |
| 59 | $C_{14}H_{24}ClNO_3$ | 58.02 | 8.35 | 4.83 | 57.68 | 8.27 | 4.81 |
| 60 | $C_{17}H_{28}ClNO_2$ | 61.90 | 8.56 | 4.25 | 61.37 | 8.44 | 4.01 |
| 61 | $C_{17}H_{25}NO_3$ | 69.59 | 9.27 | 4.77 | 69.66 | 9.24 | 4.65 |
| 62 | $C_{15}H_{20}Cl_2NO_2$ | 51.00 | 7.42 | 7.93 | 51.19 | 7.32 | 8.02 |
| 63 | $C_{17}H_{24}ClNO_3$ | 62.67 | 7.42 | 4.30 | 62.58 | 7.40 | 4.20 |
| 64 | $C_{19}H_{26}ClNO_2$ | 67.94 | 7.80 | 4.17 | 67.76 | 7.78 | 4.21 |
| 65 | $C_{12}H_{23}Cl_3N_2O_3$ | 41.22 | 6.63 | 8.01 | 42.27 | 6.27 | 8.09 |
| 66 | $C_{20}H_{28}ClNO_3$ | 65.65 | 7.71 | 3.83 | 65.37 | 7.67 | 3.75 |
| 67 | $C_{19}H_{26}ClNO_3$ | 64.86 | 7.45 | 3.98 | 64.83 | 7.35 | 4.23 |
| 68 | $C_{18}H_{29}NO_3$ | 70.32 | 9.51 | 4.56 | 70.40 | 9.58 | 4.59 |
| 69 | $C_{21}H_{34}ClNO_3$ | 65.69 | 8.93 | 3.65 | 65.78 | 8.77 | 3.60 |
| 70 | $C_{18}H_{30}ClNO_4$ | 60.07 | 8.40 | 3.89 | 60.04 | 8.28 | 3.81 |
| 71 | $C_{20}H_{28}NO_2Cl$ | 68.65 | 8.06 | 4.00 | 68.28 | 8.06 | 3.85 |
| 72 | $C_{16}H_{24}NO_2Cl$ | 64.53 | 8.12 | 4.70 | 64.40 | 8.17 | 4.55 |
| 73 | $C_{13}H_{21}Cl_2NO_2$ | 53.07 | 7.19 | 4.61 | 53.91 | 7.36 | 4.82 |
| 74 | $C_{15}H_{25}NO_2$ | 71.67 | 10.02 | 5.57 | 71.56 | 10.11 | 5.34 |
| 75 | $C_{14}H_{23}Cl_2NO_2$ | 54.55 | 7.52 | 4.54 | 54.48 | 7.52 | 4.29 |

EXAMPLE 76

1-(2-Methoxyphenoxy)-4-phthalimido-2-butanol

A mixture of 24.6 g. (0.1 mole) of 1-(2-methoxyphenoxy)-4-chloro-2-butanol, 18.5 g. (0.1 mole) of potassium phthalimido, 150 ml. of dimethylformamide and 150 ml. of toluene was refluxed for 8 hours. The cooled filtered solution was diluted with 500 ml. of water, the toluene layers separated and washed with water until the washings were neutral. The product separated from the washed toluene solution as a crystalline solid which was recrystallized from acetone. The recrystallized material melted at 108°–110° C.

Analysis: Calcd. for $C_{19}H_{19}NO_5$: C, 66.85; H, 5.61; N, 4.10. Found: C, 66.94; H, 5.74; N, 4.15.

EXAMPLE 77

1-(2-Ethoxyphenoxy)-4-phthalimido-2-butanol

A mixture of 30 g. (0.12 mole) of 1-(2-ethoxyphenoxy)-4-chloro-2-butanol and 18.5 g. (0.10 mole) of potassium phthalimide was heated slowly to 130° C. for 10 min. and at 160° C. for one hour with stirring. The reaction mixture was extracted with 250 ml. of hot toluene. A crystalline solid separated from the toluene extract when cooled to room temperature. The solid was recrystallized from toluene and melted at 93°–95° C.

Analysis: Calcd. for $C_{20}H_{21}NO_5$: C, 67.59; H, 5.96; N, 3.94. Found: C, 67.78; H, 6.03; N, 4.06.

The invention further provides pharmaceutical compositions for administration to a living animal comprising, as active ingredients, at least one of the compounds according to the invention in association with a pharmaceutical carrier or excipient. The compounds are thus presented in a form suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage unit forms according to the invention. Each dosage unit adapted for oral administration may conveniently contain 10 to 40 mg. of the active ingredient; each dosage unit adapted for intracardial or intravenous administration may conveniently contain 1 to 2 mg. per cc. of the active ingredient; whereas each dosage unit adapted for intramuscular administration may conveniently contain 5 to 10 mg. per cc. of the active ingredient.

Examples of compositions within the preferred ranges given are as follows:

| Capsules | |
|---|---|
| Ingredients | Per Cap. |
| 1. Active ingredient | 10.00 mg. |
| 2. Lactose | 146.000 mg. |
| 3. Magnesium Stearate | 4.000 mg. |

Procedure
1. Blend 1, 2 and 3.
2. Mill this blend and blend again.
3. This milled blend is then filled into #1 hard gelatin capsules.

| Tablets | |
|---|---|
| Ingredients | Mg./Tab. |
| 1. Active ingredient | 10.0 mg. |
| 2. Corn Starch | 20.0 mg. |
| 3. Kelacid | 20.0 mg. |
| 4. Keltose | 20.0 mg. |
| 5. Magnesium Stearate | 1.3 mg. |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg. |
| 2. pH 4.0 Buffer solution q.s. to | 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml. |
| 1. Active ingredient | 5.0 mg. |
| 2. Isotonic Buffer solution 4.0 q.s. to | 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredients | Per Supp. |
| 1. Active ingredient | 10.0 mg. |
| 2. Polyethylene Glycol 1000 | 1350.0 mg. |
| 3. Polyethylene Glycol 4000 | 450.0 mg. |

Procedure
1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

Pharmaceutical compositions having cardiac arrhythmia inhibiting activity and minimal $\beta$-adrenergic blocking activity, in dosage unit form, comprising a pharmaceutical carrier and a cardiac arrhythmia inhibiting amount of a compound of Formula I or a pharmaceutically acceptable acid addition salt thereof are therefore one of the objects of this invention.

Various modifications and equivalents will be apparent to one skilled in the art and may be made in the compounds, method, and compositions of the present invention without departing from the spirit or scope thereof, and it is therefore to be understood that the invention is to be limited only by the scope of the appended claims.

We claim:

1. A 1-aryloxy-4-chloro-2-butanol compound having the formula:

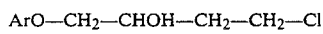

wherein Ar is 1-naphthyl, 2-naphthyl, indene-4-yl, indene-5-yl, 3-chloro-2-pyridyl, 5-chloro-2-pyridyl, or phenyl substituted with one or two radicals selected from lower alkyl, acetyl, acetylamino, halo, trifluoromethyl, and phenyl.

2. The compound of claim 1 which is 1-(2-chlorophenoxy)-4-chloro-2-butanol.

3. The compound of claim 1 which is 1-(3,5-dimethylphenoxy)-4-chloro-2-butanol.

4. The compound of claim 1 which is 1-(4-chloro-3-methylphenoxy)-4-chloro-2-butanol.

5. The compound of claim 1 which is 1-(4-chloro-2-methylphenoxy)-4-chloro-2-butanol.

6. The compound of claim 1 which is 1-(4-biphenyloxy)-4-chloro-2-butanol.

7. The compound of claim 1 which is 1-(3-trifluoromethylphenoxy)-4-chloro-2-butanol.

8. The compound of claim 1 which is 1-(4-chlorophenoxy)-4-chloro-2-butanol.

9. The compound of claim 1 which is 1-(2-methyl-5-chlorophenoxy)-4-chloro-2-butanol.

10. The compound of claim 1 which is 1-(4-acetylaminophenoxy)-4-chloro-2-butanol.

11. The compound of claim 1 which is 1-(3-chloro-2-pyridyloxy)-4-chloro-2-butanol.

12. The compound of claim 1 which is 1-(5-chloro-2-pyridyloxy)-4-chloro-2-butanol.

13. The compound of claim 1 which is 1-(3-chlorophenoxy)-4-chloro-2-butanol.

14. The compound of claim 1 which is 1-(4-acetylphenoxy)-4-chloro-2-butanol.

15. The compound of claim 1 which is 1-(o-phenylphenoxy)-4-chloro-2-butanol.

* * * * *